ated Patent [19] [11] Patent Number: 5,260,396
Kroner et al. [45] Date of Patent: Nov. 9, 1993

[54] PREPARATION OF WATER RESISTANT FILMS AND COATINGS AND USE THEREOF

[75] Inventors: Matthias Kroner, Bad Durkheim; Heinrich Hartmann, Limburgerhof; Ekhard Winkler, Mutterstadt; Juergen Steinmetz, Boehl-Iggelheim; Thomas Anstock, Weisenheim, all of Fed. Rep. of Germany

[73] Assignee: BASF Aktiengesellschaft, Ludwigshafen, Fed. Rep. of Germany

[21] Appl. No.: 970,246

[22] Filed: Nov. 2, 1992

Related U.S. Application Data

[63] Continuation of Ser. No. 842,992, Feb. 28, 1992, abandoned.

[30] Foreign Application Priority Data

Mar. 14, 1991 [DE] Fed. Rep. of Germany ....... 4108170

[51] Int. Cl.⁵ .................. C08H 89/00; B32B 7/00; B32B 27/00
[52] U.S. Cl. ................... 527/201; 523/100; 428/245; 428/290; 428/478.2; 428/478.8; 428/911; 604/358; 604/372; 604/373

[58] Field of Search .......... 527/201; 523/100; 428/245, 290, 478.2, 478.4, 478.8, 911; 604/358, 372, 373

[56] References Cited

U.S. PATENT DOCUMENTS 2,956,884 10/1960 Caldwell .................. 526/322
3,651,210 3/1972 Shepler et al. ............ 523/122
4,812,550 3/1989 Erickson et al. .......... 527/201

FOREIGN PATENT DOCUMENTS 545084 8/1957 Canada .................. 527/201
644570 7/1962 Canada .................. 527/201

Primary Examiner—Nathan M. Nutter
Attorney, Agent, or Firm—Oblon, Spivak, McClelland, Maier & Neustadt

[57] ABSTRACT

Water resistant films and coatings are prepared by treating films or coatings of water soluble or dispersible grafted proteins prepared with monoethylenically unsaturated monomers at above 40° C. and/or with at least one compound which is a hardener for proteins, and are useful as compostable packaging materials or as outer layers of diapers.

4 Claims, No Drawings

PREPARATION OF WATER RESISTANT FILMS AND COATINGS AND USE THEREOF

This application is a continuation of application Ser. No. 07/842,992, filed on Feb. 28, 1992, now abandoned.

The present invention relates to a process for preparing water resistant films and coatings from water soluble or dispersible grafted proteins obtainable by free radical initiated polymerization of (a) monoethylenically unsaturated monomers in the presence of (b) proteins in a weight ratio of (a):(b) of (from 0.5 to 90):(from 99.5 to 10).

U.S. Pat. No. 4,812,550 discloses a process for preparing grafted proteins wherein ethylenically unsaturated monomers having not more than 14 carbon atoms in the molecule are subjected to a free radical polymerization in an aqueous medium in the presence of solubilizing proteins. The latices thus obtainable are used as binders for pigmented paper coating compositions.

U.S. Pat. No. 2,956,884 discloses polymerizing acrylic esters or acrylonitrile in the presence of crosslinking agents such as divinylbenzene, diallyl phthalate or acrylic esters of glycols and also in the presence of gelatin. The reaction mixtures thus obtainable can be used to cast films or prepare coatings on textiles or paper. Owing to the presence of crosslinker as copolymerized units, the coatings and films are water insoluble. The water insolubility of the films and coatings can be increased still further by treating the polymer compositions with curing agents for gelatin, for example with formaldehyde, N-methylolurea, trimethylolmelamine and aluminum salts.

U.S. Pat. No. 3,651,210 discloses that reactive synthetic polymer latices which contain glycidyl esters of $\alpha,\beta$-ethylenically unsaturated carboxylic acids as copolymerized units can, on completion of their preparation, be linked to water soluble proteins. The products thus obtainable can be cured at room or elevated temperature by the action of air. The products obtainable by chemical reaction of reactive synthetic polymer latices and proteins are for example binders for fiber webs and coating agents for preparing leather substitute materials. They are also suitable for preparing films, which may optionally be cured. Owing to the protein content, the reaction products of reactive latex and protein are biodegradable.

Commercially available disposable diapers consist essentially of a water permeable fleece lining, which forms the inner layer of the diaper, and a water impermeable sheet as outer layer. Between the inner and outer layer are water absorbent materials, e.g. fluff, and frequently additionally also superabsorbers, i.e. polymers with a high absorption capacity for water. After use, these diapers are normally disposed of, together with other household refuse, in incinerators or by landfilling. The utilization of used diapers as biowaste or as a component in biowaste would be a more elegant method of disposal, but this is where in particular the outer sheet presents problems, since in general it is made of a material which will not rot.

To be able to use conventional disposable diapers as a component in biowaste nonetheless, the diaper must be mechanically comminuted or the film must first be expensively separated off and disposed of separately. However mechanical comminution results in comparatively large film shreds, the presence of which makes spreading the biowaste difficult and is later also undesirable in soil.

It is an object of the present invention to provide a process for preparing water resistant films and coatings which are suitable for composting. These films or coatings shall be usable in particular for the outer layer of throwaway diapers.

We have found that this object is achieved by a process for preparing water resistant films and coatings from water soluble or dispersible grafted proteins obtainable by free radical initiated polymerization of (a) monoethylenically unsaturated monomers in the presence of (b) proteins in a weight ratio of (a):(b) of (from 0.5 to 90):(from 99.5 to 10) by conferring water resistance on films or coatings which are each obtainable from the water soluble or dispersible grafted proteins by heat treatment at above 40° C. or treatment with at least one compound which is a hardener for proteins. The water resistant films and coatings thus obtainable can be employed as packaging materials or as outer layer of disposable diapers. Although these coatings and films are water resistant they are also compostable. A further advantage of these coating materials and films is that they dissolve relatively rapidly at an alkaline pH.

The preparation of grafted proteins is known: cf. above-cited U.S. Pat. No. 2,956,884. As component (a) it is possible to use any monoethylenically unsaturated monomer. Examples are monoethylenically unsaturated $C_3$–$C_8$-carboxylic acids, such as acrylic acid, methacrylic acid, ethacrylic acid, crotonic acid, maleic acid, fumaric acid, itaconic acid, aconitic acid and vinylacetic acid. It is also possible to use, if industrially available, the corresponding anhydrides, e.g. maleic anhydride or itaconic anhydride. Of the aforementioned compounds, preference is given to acrylic acid, methacrylic acid and mixtures thereof. The carboxylic acids can be used in the graft copolymerization as free carboxylic acids or in the form of salts with inorganic or organic bases. To neutralize the monoethylenically unsaturated carboxylic acids it is possible to use for example sodium carbonate, sodium bicarbonate, potassium carbonate, potassium bicarbonate, sodium hydroxide solution, potassium hydroxide solution, alkaline earth metal oxides and hydroxides, ammonia, trimethylamine, triethylamine, tributylamine, triethanolamine, diethanolamine, morpholine, methylamine or dimethylamine. For neutralization purposes it is also possible to use mixtures of various bases, for example sodium hydroxide solution and ammonia.

Suitable compounds of group (a) also include the esters of the abovementioned carboxylic acids with monohydric or polyhydric $C_1$–$C_{22}$-alcohols. Suitable alcohols for esterifying the above-described monoethylenically unsaturated carboxylic acids are for example methanol, ethanol, n-propanol, isopropanol, n-butanol, isobutanol, tert-butanol, 2-ethylhexyl alcohol, stearyl alcohol, palmityl alcohol, decyl alcohol, dodecyl alcohol, tallow fat alcohol, sorbitol, mannitol, glycerol, ethylene glycol, propylene glycol and butanediol. Preference is given to using the esters of acrylic acid and methacrylic acid with methanol, ethanol, n-propanol, n-butanol, tert-butanol, 2-ethylhexyl alcohol, stearyl alcohol, ethylene glycol and propylene glycol. Of the esters mentioned, particular preference is given to n-butyl acrylate, methyl methacrylate, ethylhexyl acrylate and ethyl acrylate alone or mixed with acrylic acid and/or methacrylic acid for the graft copolymerization in the presence of proteins.

Other suitable monomers of group (a) are the amides of $C_3-C_8$-carboxylic acids which are derived from ammonia, $C_1-C_{22}$-alkylamines or dialkylamines. Suitable amines for preparing the amides are for example methylamine, dimethylamine, stearylamine, tallow fat amine and palmitylamine. It is also possible to use the N-methylol derivatives of amides, for example N-methylolacrylamide or N-methylolmethacrylamide. The aforementioned N-methylol derivatives of the amides may also be etherified, for example with $C_1-C_{22}$-alcohols, preferred monomers being N-(butoxymethyl)acrylamide and N-(isobutoxymethyl)acrylamide.

Other suitable monomers (a) are the nitriles of carboxylic acids, such as acrylonitrile or methacrylonitrile, vinyl ethers of alcohols containing from 1 to 18 carbon atoms, e.g. vinyl methyl ether, vinyl isobutyl ether, vinyl n-butyl ether and vinyl ether ether, and also vinyl esters of saturated $C_1-C_4$-carboxylic acids, in particular vinyl acetate, vinyl propionate and vinyl butyrate. Other suitable monomers are styrene and alkyl-styrenes. The graft copolymers contain the monomers (a) in copolymerized form in amounts of from 0.5 to 90, preferably from 10 to 85%, by weight.

The other essential component of the graft copolymerization is a protein (b). For this purpose it is possible to use any protein which, under the conditions of the polymerization, is soluble in the polymerization medium in a proportion of at least 20% by weight. Suitable proteins are described for example in above-cited U.S. Pat. No. 4,812,550. A further survey of suitable proteins may be found in Ullmanns Enzyklopldie der technischen Chemie, 4th Edition, Weinheim 1980, Volume 19, 491-557. The proteins in question are sustainable raw materials. They are derived for example from skin, hides, supportive and connective tissue, bones and cartilage: collagen, elastin, gelatin, ossein and glue. Protein from milk are whey proteins, casein and lactalbumin. Wool, bristles, feathers and hairs are the source of keratin. It is also possible to use proteins from fish and eggs and from blood as slaughterhouse waste, for example blood proteins, albumen, globulin, globin, fibrinogen and hemoglobin. Other suitable proteins come from plants, such as corn, wheat, barley, oats and potatoes: glutelin, prolamin, zein and gluten. It is also possible to obtain proteins from seeds, for example from soybeans, cotton seeds, peanuts, sunflower seeds, rapeseed, coconut, linseed, sesame, safflower, peas, beans and lentils. It is also possible to use the protein constituents of clover, lucerne, grass, potatoes, maniac and yam. Further protein sources are bacteria, fungi, algae and yeasts, e.g. Pseudomonas, Lactobacillus, Penicillium, blue algae, green algae, Chlorella, Spirulina and exhausted yeast. The proteins which are preferred for use as component (b) for preparing the graft copolymers are casein, gelatin, bone glue and proteins from soybeans, cereals, in particular wheat and corn, peas and potatoes. The proteins are for example isolated from the natural raw materials by dissolving, grinding, sifting and classifying. To convert them into a soluble form, they need in many cases to be subjected to a digestive process in the form of a physical, chemical or enzymatic treatment, for example hydrolysis with acid or alkali, fermentation with yeasts, bacteria or enzymes, extraction methods for removing concomitants, coagulation from extracts by heat, addition of electrolyte, pH change or addition of coagulants. To obtain pure products, a possible option is for example fractional dissolving and precipitating and a dialysis process.

In the copolymerization, (a) the monoethylenically unsaturated monomers are used in the presence of (b) proteins in a weight ratio of (a):(b) of (0.5-90):(99.5-10), preferably (10-85):(90-15).

The monomers (a) are polymerized in the presence of proteins by a free radical mechanism. The free radical donor can be any compound known for this purpose. This initiator may be soluble or else insoluble in water. Water soluble initiators are for example inorganic peroxides, such as potassium peroxodisulfate, sodium peroxodisulfate, ammonium peroxodisulfate and hydrogen peroxide. It is also possible to use organic peroxides, hydroperoxides, peracids, ketone peroxides, perketals and peresters, e.g. methyl ethyl ketone hydroperoxide, cumene hydroperoxide, tert-butyl hydroperoxide, 1,1-di(tertbutylperoxy)cyclohexane, di(tert-butyl) peroxide, tertbutyl peroxypivalate, tert-butyl monoperoxymaleate, dicyclohexyl peroxydicarbonate, dibenzoyl peroxide, diacetyl peroxide, didecanoyl peroxide and mixtures thereof. It is also possible to use redox systems which combine a peroxy compound with a reducing component. Suitable reducing components are for example cerium(III) and iron(II) salts, sodium sulfite, sodium hydrogen sulfite, sodium dithionite, ascorbic acid and sodium formaldehydesulfoxylate. The initiator chosen is preferably a compound which forms free radicals and has a half-life of less than 3 hours at the particular chosen polymerization temperature. If the polymerization is started at a low temperature and completed at a higher temperature, it is advantageous to use at least two initiators which decompose at different temperatures, namely an initiator which decomposes at a low temperature for the start of the polymerization and then an initiator which decomposes at a high temperature for the completion of the main part of the polymerization. By adding heavy metal salts, for example copper, cobalt, manganese, iron, nickel and chromium salts to peroxidic catalysts it is possible to reduce the decomposition temperature of the latter. Suitable initiators also include azo compounds, such as 2,2'-azobisisobutyronitrile, 2,2'-azobis(2-amidinopropane) dihydrochloride, 2,2'-azobis(2-methylpropionamidine) dihydrochloride, 2,2'-azobis(2,4-dimethylvaleronitrile) and dimethyl 2,2'-azobisisobutyrate. Particular preference is given to using hydrogen peroxide, potassium peroxodisulfate, ammonium peroxodisulfate and sodium peroxodisulfate and tert-butyl perpivalate as initiator in the graft polymerization. Based on the monomers to be polymerized, the amount of initiator or initiator mixture used is from 0.5 to 10, preferably from 1 to 8%, by weight. The amount of initiator used can have an appreciable bearing on the graft polymer which is formed.

If water insoluble monomers are used in the graft polymerization, it is possible to obtain polymers having particularly advantageous properties by first adding a water soluble initiator for the main reaction and then a water insoluble initiator for completing the polymerization and removing remaining monomers from the latex. However, it can also be advantageous to introduce a fraction of the total amount of initiator required at the start of the polymerization and to add the remainder continuously or batchwise over a period of from 10 minutes to 10 hours, preferably from 1 to 3 hours. This is particularly advantageous in the case of monomers which are slow to polymerize and for reducing the residual monomer content of the graft polymer. If the monomers and the initiator are metered simultaneously into a polymerizing mixture, it is advantageous to add the initiator over a period which is from 10 minutes to 2 hours longer than the period over which the monomers are added. For instance, the time for adding the monomers may be 2 hours and for the initiator 3 hours.

The graft polymerization may, if desired, be carried out in the presence of regulators. Suitable regulators are for example mercapto compounds, such as mercaptoethanol, mercaptopropanol, mercaptobutanol, mercaptoacetic acid, mercaptopropionic acid, butylmercaptan and dodecylmercaptan. Suitable regulators also include allyl compounds, such as allyl alcohol, aldehydes such as formaldehyde, acetaldehyde, propionaldehyde, n-butyraldehyde and isobutyraldehyde, formic acid, ammonium formate, propionic acid, hydroxylamine sulfate and butenols. If the graft copolymerization is carried out in the presence of regulators, they may be used in amounts of from 0.05 to 20% by weight, based on the monomers used in the polymerization.

The polymerization can be carried out in an aqueous medium or in an organic solvent in which the proteins are soluble to at least 20% by weight. Suitable organic solvents are for example acetic acid, formic acid, alcohols, such as methanol, ethanol, n-propanol, isopropanol, n-butanol, tert-butanol and isobutanol, and ethers, such as tetrahydrofuran and dioxane. It is also possible to use ketones, such as acetone and methyl ethyl ketone, as inert diluents in the graft polymerization. Particular preference is given to the use of methanol, ethanol, isopropanol, acetone, tetrahydrofuran and dioxane. The graft polymerization can be carried out in mixtures of organic solvents and also in mixtures of water and organic solvents which are soluble in water. The concentration of monomer and protein in the particular solvent used is from 10 to 70, preferably from 15 to 60%, by weight.

The graft polymerization is carried out in customary apparatus equipped with mixing elements, for example in stirred flasks, kettles, autoclaves and cylindrical reactors. The graft polymerization may also be carried out in kettle cascades or in other interconnected polymerization apparatus. The polymerization may be carried out batchwise or continuously. Suitable polymerization apparatus also includes kneaders. If water soluble monomers (a) are used in the graft polymerization, the polymerization may also be carried out as a reverse suspension polymerization or as a water-in-oil emulsion polymerization. Preferably, the graft polymerization takes the form of a solution polymerization or emulsion polymerization. If it is carried out as an emulsion polymerization, it is also possible to add the emulsifiers and protective colloids in amounts of up to 5% by weight. Preferably, however, no surface-active additives are present. For specific applications it may be useful to employ a precipitation polymerization. The polymerization need not be initiated solely with free radical initiators, but may also be initiated by the action of UV radiation or by the action of high-energy rays, for example $\alpha$- or $\beta$- or $\gamma$-rays. The graft polymerization is carried out within the temperature range from 20° to 160° C., preferably from 30° to 100° C. In the case of temperatures which are above the boiling point of the particular solvent used, the graft polymerization is customarily carried out in pressure-tight apparatus. The polymerization is preferably carried out in an inert gas atmosphere in the absence of atmospheric oxygen, for example by using nitrogen, argon, helium or carbon dioxide as inert gas. The reaction temperature and the amount of initiator have a bearing on the properties of the graft polymers formed.

In the case of relatively small polymerization batches, where the heat of polymerization can be removed sufficiently rapidly, the monomers to be polymerized and the protein can be introduced into the reaction vessel at the start together with at least one polymerization initiator and polymerized by heating to the particular polymerization temperature required. It is more advantageous, however, to charge the polymerization apparatus with only a portion of the monomer (a) and a portion of the initiator as well as all of the protein (b) and to add the remaining monomer (a) and initiator continuously or batchwise at a rate commensurate with the rate of polymerization. The order in which the reactants are metered into the polymerization reactor can be freely varied. For instance, it is possible to heat a solution or dispersion of the protein in the reactor to the required polymerization temperature and to add the monomers and initiators continuously or batchwise. If a plurality of monomers are used in the graft polymerization, the individual monomers can be metered into the polymerization zone in succession, or as a mixture or else simultaneously from separate metering means. In the case of relatively large polymerization batches and preferably in the case of water insoluble monomers (a) it can be advantageous to prepare a mixture of water, solvents, regulators, bases and the total amounts of monomers (a) and proteins (b) and to meter this mixture in the polymerization vessel continuously or batchwise, simultaneously with the initiator, at a rate commensurate with the rate of polymerization.

Similarly, the pH of the reaction medium can have a bearing on the properties of the graft polymer. The solubility of the proteins below and above the isoelectric point can be utilized in the graft polymerization. Acidic or basic monomers can be used in the form of the corresponding salts. For instance, acrylic acid is employed in the form of a free acid or in the form of the ammonium or an alkali or alkaline earth metal salt. The graft polymerization can be carried out within the pH range from 1 to 14, preferably from 6 to 12. By changing the pH it is possible for example to precipitate the graft polymers from solutions. This possibility may be employed when working up, purifying and isolating the graft copolymers. It can be of advantage to use two or more proteins in the graft polymerization. The order in which these proteins are used can have favorable effects on the properties of the graft copolymers formed. In some cases it is of advantage to utilize the emulsifying power of protein by first emulsifying a water insoluble monomer with a protein and then adding a further protein and subjecting the reaction mixture to the graft copolymerization. In the case of water insoluble monomers, for example n-butyl acrylate, N-butoxymethylacrylamide, N-isobutoxymethylmethacrylamide, 2-ethylhexyl acrylate or methyl methacrylate, it is possible, in a preferred embodiment, first to prepare a three-phase mixture of monomer, water and insoluble protein, e.g. casein. Then the protein is dissolved by adding an alkali, for example sodium hydroxide solution, potassium hydroxide solution, ammonia solution, triethylamine, alkanolamine, morpholine or some other alkaline substance. The emulsifying effect of the protein being dissolved is particularly good with this method.

To keep the graft copolymers, for example of casein, in a state of solution or dispersion in water, a base is used for neutralization. As neutralization bases for the protein, and thus also for the graft copolymers obtained therefrom, it is possible to use not only sodium hydroxide solution, potassium hydroxide solution, sodium carbonate, potassium carbonate, sodium bicarbonate or potassium bicarbonate but also volatile mono-, di- or tri-$C_1$-$C_{18}$-alkylamines or nitrogen-containing heterocyclic bases. The boiling points of the volatile neutralization bases are within the range from $-34°$ C. to 200° C., preferably from $-34°$ C. to 130° C.

Examples are ammonia, methylamine, dimethylamine, trimethylamine, ethylamine, diethylamine, triethylamine, tributylamine, ethylisopropylamine, ethyl diisopropylamine, diisopropylamine, morpholine, N-methylmorpholine, piperazine, N,N-dimethylpiperazine, 1-methoxy-2-aminopropane, ethylaminoethylamine, N,N-dimethylethylenedismine, 2-dimethylaminoethylamine, cyclopropylamine, cyclopentylamine, cyclohexylamine, aniline, dimethylaniline, toluidine, quinoline, isoquinoline and pyridine.

The proteins used in the graft copolymerization may be chemically modified in various ways before or after the graft polymerization. For example, it can be of advantage to partially degrade the protein before the polymerization by hydrolytic or enzymatic means. Depending on the reaction conditions, a partial hydrolytic degradation of the proteins may take place during the graft polymerization. After the graft polymerization the graft polymers may be modified in various ways, for example graft polymers of alkyl acrylates on proteins may be hydrolyzed with elimination of an alcohol.

Similarly, before or after the free radical grafting, functional groups of the proteins can be reacted with reactive carboxylic acid derivatives, for example carboxylic anhydrides. Examples of carboxylic anhydrides are acetic anhydride, succinic anhydride and maleic anhydride. N-(Alkyloxymethyl)carbonamide-containing graft polymers may be reacted under acidic conditions with protein fractions.

The grafted proteins thus obtainable with monoethylenically unsaturated monomers either in dissolved or dispersed form have K values of from 10 to 200, preferably from 15 to 180 (determined by the method of H. Fikentscher in 1% solution in water at 25° C. and pH 7). In the closed bottle test the graft copolymers show a degree of biodegradability which corresponds to the protein content, and in the Zahn-Wellens elimination test they are more than 85% eliminable. If they are to be stored in the presence of water, a commercial preservative is used. In the air-dried state, the graft polymers have long storage lives even without preservatives.

The graft polymers described are used for preparing films and as coating agents for paper, fleeces and fabrics. Fleeces are materials made of cellulose fibers, for example cotton, staple viscose, linen, jute and ramie; and polyester-cellulose fiber blends, polyesters, polyacrylonitrile, filament viscose, wool, polyester-wool blends, acetate, triacetate and polyamide. The fleeces may also be composed of multilayered strata of various materials. For instance, between 2 cellulose layers there may be incorporated a tear resistant fabric of polyamide. The graft polymers can be used not only alone but also together with other components. Moreover, they can be mixed with one another in any desired proportion.

The preparation of films is effected for example by casting solutions or dispersions of the graft copolymers onto planar surfaces and then evaporating the solvent. The temperatures for this may be up to 200° C. The solvents are preferably removed with the aid of a gas stream or under reduced pressure.

Coatings on paper, fleeces and fabrics are prepared for example by dipping the materials into an aqueous dispersion or solution of the graft copolymers and then drying. This operation can be repeated several times. Particularly water resistant films are obtained on heat treating the coated materials at from 40° to 200° C., preferably above 50° C. The heat treatment is particularly preferably carried out within the range from 70° to 150° C. At 100° C. the heat treatment takes for example from 30 minutes to 3 hours. The higher the temperature, the shorter the treatment time. By repeatedly dipping and drying the fleeces it is possible to produce multilayered water resistant coatings. The coatings can of course also be obtained by spraying with finely atomized solutions or dispersions of the above-described graft copolymers. This technique is used in particular on continuous ranges. The amount of graft copolymer applied to paper or fleece is preferably from 0.1 to 5 times the weight of the substrate to be coated. This produces coatings with a polymer addon of about 1-300 g/$m^2$. In the course of the preparation of films or coatings it is also possible to incorporate pigments, opacifiers and dyes.

The films and coatings are made water resistant either by heat treating them at above 50° C. for a sufficiently long time and optionally additionally or exclusively treating them with at least one compound which is a hardener for proteins. If volatile bases such as ammonia or amines were used for neutralizing the graft copolymers, water resistance of the films and coatings is achievable by heat treatment at over 50° C. alone. The coated materials may be heated to the temperature required for rendering the graft copolymers water resistant by placing them in a hot gas stream or else by treating them at elevated temperature under reduced pressure. Water resistance of the films and coatings is also achievable by treatment with compounds which are hardeners for proteins. Such hardeners are for example formaldehyde, formaldehyde donor compounds, acids and at least divalent salts. Suitable acids include not only inorganic but also organic acids, e.g. halohydric acids, in particular hydrochloric acid, phosphoric acid, sulfuric acid and nitric acid and also for example formic acid, acetic acid, propionic acid, p-toluenesulfonic acid, benzenesulfonic acid, acrylic acid and succinic acid. For example, a film or coating of a graft polymer of n-butyl acrylate on casein which has been neutralized with sodium hydroxide solution can be rendered water resistant by storing the film or coating for from 10 to 90 minutes in an atmosphere of air saturated with formic acid.

Suitable hardeners for proteins also include solutions of at least divalent metal salts. Such salts contain for example the following cations: $Ca^{2+}$, $Al^{3+}$, $Fe^{2+}$, $Ba^{2+}$, $Zn^{2+}$, $Cu^{2+}$ and $Ni^{2+}$. Suitable salts of this kind are for example barium chloride, calcium chloride, calcium acetate, iron(II) sulfate, potassium aluminum sulfate, nickel sulfate, zinc chloride, copper sulfate and copper chloride. Particular preference is given to aluminum, calcium and iron ions in the form of calcium chloride, calcium acetate, iron sulfate, potassium aluminum sulfate and aluminum sulfate. The films and coatings of proteins grafted with monoethylenically unsaturated compounds can also be made water resistant by treatment with formaldehyde and/or formaldehyde donor compounds, e.g. N-methylolurea, methylolmelamine, trioxane and paraformaldehyde. Preference is given to using formaldehyde and also glyoxal or glutaraldehyde. It is of course possible to use mixtures of various aldehydes and aldehydes combined with a metal salt or a plurality of the abovementioned metal salts. Whether a compound is a suitable hardener for proteins is readily ascertainable, for example by combining an aqueous solution of casein with an aqueous solution of the compound to be tested. If a precipitate forms, the compound is a suitable hardener for protein. The films and coatings of grafted protein are contacted with such an amount of hardener as to produce water resistant films and coatings. The amount is customarily from 1 to 1000 g/100 g of graft protein to be rendered water resistant. The treatment with hardeners for proteins can be carried out within a wide temperature range, for example at from 5° to 200° C., preferably at from 10° to 70° C. The treatment is complete within 10 minutes to 24 hours. Water resistant films of the originally water soluble or dispersible grafted proteins are used as compostable packaging materials, for example for manufacturing bags or carrier bags. The coated substrates, such as paper, fleeces or fabrics based on cellulose fibers, are also used as packaging materials which are compostable. Particular preference is given to using the grafted proteins which have been rendered water resistant as outer layer of diapers. The diapers contain as outer layer either a film or coating of an originally water soluble or dispersible grafted protein which has been rendered water resistant. The outer layer of the diaper effectively prevents the leakage of urine absorbed on the inside of the diaper by fluff with or without superabsorbers, based for example on crosslinked polyacrylic acid or crosslinked polyacrylamide. The inner layer of the diaper is usually a fibrous fleece liner made of a cellulose material. The outer layer of the diapers described is at least partly biodegradable and hence compostable. It disintegrates in the course of being composted, so that the entire diaper rots, while a diaper with polyethylene on the outside is not compostable without the special treatment described earlier.

The K values of the graft copolymers were determined by the method of H. Fikentscher, Cellulosechemie, 13 (1932), 58–64, 71–74. The measurements were carried out on 1% strength by weight aqueous solutions of the graft copolymers at 25° C. and pH at 7. The percentages are by weight. The preservative used for the aqueous solutions and dispersions of the graft polymers was Proxel ® XL 2 in the form of a 10% strength aqueous solution.

EXAMPLES

Preparation of graft polymers

Graft polymer 1

In a 2 l capacity glass apparatus equipped with a horseshoe stirrer, feed means for monomers, initiator solutions and sodium hydroxide solution, a reflux condenser and nitrogen inlet and outlet, 120 g of casein (in the acid form) and 500 g of water are suspended at 20° C. under nitrogen. 180 g of n-butyl acrylate are then added in one portion, and the mixture is subsequently stirred at 20° C. for 15 minutes. Then 9 g of 25% aqueous ammonia solution are added dropwise in the course 15 minutes. On completion of the addition of ammonia the mixture is further stirred at 20° C. for 40 minutes. Then 20 g of 13% aqueous sodium peroxodisulfate solution are added in one portion and the temperature of the reaction mixture is raised to 75° C. As soon as that temperature is reached, 20 g of 10% aqueous sodium peroxodisulfate solution are added in the course of 2 hours and, after all the initiator has been added, the reaction mixture is stirred at 70° C. for a further 2 hours. Then 1 g of tert-butyl perpivalate is added and stirring is continued at 75° C. for a further 2 hours. 1 g of the preservative is then added to give a white latex having a solids content of 35%. The K value of the grafted polymer is 23.2. The polymer has a residual monomer content of 0.01% of n-butyl acrylate.

Graft polymer 2

In a 2 l capacity glass apparatus equipped with a horseshoe stirrer, feed means for monomers, initiator solutions and sodium hydroxide solution, a reflux condenser and nitrogen inlet and outlet, 120 g of casein (in the acid form) and 500 g of water are suspended at 20° C. under nitrogen. Then 180 g of n-butyl acrylate are added in one portion, and the mixture is stirred at 20° C. for 15 minutes. Then 32 g of 12.5% aqueous sodium hydroxide solution are added dropwise in the course of 15 minutes. After the sodium hydroxide solution has been added the mixture is stirred at 20° C. for 40 minutes. Then 100 g of 3% aqueous potassium peroxodisulfate solution are added in one portion and the temperature of the reaction mixture is raised to 75° C. As soon as that temperature has been reached, 70 g of 3% aqueous potassium peroxodisulfate solution are metered in over 2 hours and, after all the initiator has been added, the reaction mixture is stirred at 70° C. for a further 4 hours. 1 g of the preservative is added to obtain a white latex having a solids content of 29%. The K value of the grafted polymer is 20.8. The polymer has a residual monomer content of 0.03% of n-butyl acrylate.

USE EXAMPLES

Two different kinds of cellulose material were used as fiber mat fleece.

Paper 1 was a single-layered teabag paper cellulose material having a specific weight of 37 g/m².

Paper 2 was a double-layered cellulose material having a specific weight of 57 g/m².

The paper materials were each cut to a format of 21×10 cm and dipped into aqueous dispersions of graft polymer 1. After dipping, the sheets were suspended to allow excess coating dispersion to drip off. After drying at 20° C. for 3 hours the coated sheets of paper were dipped once more and then stored in a drying cabinet at the temperatures indicated in the table. For this the storage times and temperatures were chosen in such a way that the coated papers became resistant and non-wetting to water. The cellulose materials repeatedly treated with aqueous graft polymers were dried at 20° C. for 3 hours after every dip. The experimental conditions and results are indicated in the table.

TABLE

| Example | Paper | Concentration of aqueous dispersion of graft polymer 1 [%] | Number of dips | Drying Time [h] | Drying Temp. [°C.] | Addon of water resistant graft polymer 1 [g/m²] | Addon of water resistant graft polymer 1 [%] |
|---|---|---|---|---|---|---|---|
| 1 | 1 | 10 | 1 | 2 | 100 | 8 | 26 |

TABLE-continued

| Example | Paper | Concentration of aqueous dispersion of graft polymer 1 [%] | Number of dips | Drying Time [h] | Drying Temp. [°C.] | Addon of water resistant graft polymer 1 [g/m²] | Addon of water resistant graft polymer 1 [%] |
| --- | --- | --- | --- | --- | --- | --- | --- |
| 2 | 2 | 20 | 3 | 3 | 100 | 180 | 354 |
| 3 | 2 | 20 | 3 | 2 | 100 | 154 | 305 |
| 4 | 2 | 15 | 1 | 2 | 100 | 26 | 45 |
| 5 | 2 | 15 | 2 | 2 | 100 | 54 | 96 |
| 6 | 2 | 15 | 3 | 2 | 100 | 96 | 170 |
| 7 | 2 | 15 | 1 | 1 | 120 | 28 | 49 |
| 8 | 2 | 15 | 2 | 1 | 120 | 58 | 100 |
| 9 | 2 | 15 | 3 | 1 | 120 | 50 | 160 |
| 10 | 2 | 15 | 1 | 3 | 100 | 26 | 45 |
| 11 | 1 | 15 | 1 | 1 | 120 | 14 | 39 |
| 12 | 1 | 15 | 2 | 1 | 120 | 23 | 68 |
| 13 | 1 | 15 | 1 | 2 | 100 | 11 | 29 |
| 14 | 1 | 15 | 2 | 2 | 100 | 23 | 68 |

The above-described coated fibrous fleece mats were water resistant at a pH of 7 or below. In contrast, at pH 8-10 they dissolved after about 20 minutes.

EXAMPLE 15

The above-described paper 2 was cut to a size of 23×8 cm and dipped into a 20% aqueous dispersion of graft polymer 2, then incipiently dried freely hanging at 20° C. for 2 hours, dipped again and dried thoroughly by hanging overnight at 20° C. The polymer addon was 4.15 g, corresponding to 456%, based on the uncoated paper. The addon was 218 g/m². On dipping the coated fleece into water, the coating was easy to wash off. However, to convert the coating into a water resistant form, the coated paper 2 was hung up for 1 hour in a sealable chamber whose gas space was saturated with formic acid. The fleece was then air dried overnight. The coating turned water resistant.

EXAMPLE 16

Example 15 was repeated, except that the paper was dipped into a 10% aqueous calcium chloride solution. After 1 hour it was removed, placed in a bowl of water for 30 minutes with occasional swirling, and then dried. The paper had a water resistant coating.

EXAMPLE 17

A fleece coated as in Example 15 was placed in a 10% aqueous glyoxal solution. After a residence time of 1 hour it was removed therefrom, washed with water and dried. The coating had turned water resistant in that time.

EXAMPLE 18

A 29% dispersion of graft polymer 1 was applied to a release paper with the aid of a commercial coating machine in the following layer thicknesses:
(a) 20 μm
(b) 40 μm
(c) 100 μm.

Drying the applied graft polymer dispersions at 120° C. in a drying cabinet to constant weight gave virtually transparent peelable films which became water resistant after drying for 3 hours.

EXAMPLE 19

A 30% dispersion of graft polymer 2 was applied to a release paper with a commercial coating machine in a thickness of 40 μm and air dried overnight. The transparent film was peeled off the release paper and suspended for 1 hour in a chamber saturated with formic acid. The film was then thoroughly washed with water and hung up to dry at 20° C. The acid treatment had made it water resistant.

The coatings prepared as described in Examples 15 to 17 were usable as outer layers of diapers. The films obtained according to Examples 18 and 19 were likewise used as outer layers of diapers.

We claim:

1. A process for preparing a water resistant film or coating from a water soluble or dispersible grafted protein comprising
   A) polymerizing by a free radical mechanism a mixture consisting essentially of (a) a monoethylenically unsaturated monomer and (b) a protein in a weight ratio of (a):(b) of (from 0.5 to 90):(from 99.5 to 10) to form a grafted protein,
   B) forming a film or coating from the grafted protein, and
   C) treating the film or coating with at least one compound selected from the group consisting of acids, di- or tri-valent salts, glyoxal or glutaraldehyde.

2. A process as claimed in claim 1, wherein the coating is prepared on paper or a fibrous mat.

3. A method of packaging a material, comprising packaging the material with a compostible packaging film or coating prepared by
   A) polymerizing by a free radical mechanism a mixture consisting essentially of (a) a monoethylenically unsaturated monomer and (b) a protein in a weight ratio of (a):(b) of (from 0.5 to 90):(from 99.5 to 10) to form a grafted protein,
   B) forming a film or coating from the grafted protein, and
   C) treating the film or coating with at least one compound selected from the group consisting of acids, di- or tri-valent salts, glyoxal or glutaraldehyde.

4. A diaper containing as outer layer a film or coating prepared by
   A) polymerizing by a free radical mechanism a mixture consisting essentially of (a) a monoethylenically unsaturated monomer and (b) a protein in a weight ratio of (a):(b) of (from 0.5 to 90):(from 99.5 to 10) to form a grafted protein,
   B) forming a film or coating from the grafted protein, and
   C) treating the film or coating with at least one compound selected from the group consisting of acids, di- or tri-valent salts, glyoxal or glutaraldehyde.

* * * * *